(12) United States Patent
Otwinowski et al.

(10) Patent No.: US 10,100,347 B2
(45) Date of Patent: Oct. 16, 2018

(54) MAPPING CELL IDENTITY DETERMINANTS IN CHROMATIN

(71) Applicant: Board of Regents, The University of Texas System, Dallas, TX (US)

(72) Inventors: Zbyszek Otwinowski, Dallas, TX (US); Dominika Borek, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 345 days.

(21) Appl. No.: 15/139,318

(22) Filed: Apr. 26, 2016

(65) Prior Publication Data

US 2016/0312267 A1    Oct. 27, 2016

Related U.S. Application Data

(60) Provisional application No. 62/152,926, filed on Apr. 26, 2015.

(51) Int. Cl.
  *C12Q 1/6806* (2018.01)
  *C12Q 1/6855* (2018.01)
  *C12Q 1/6869* (2018.01)

(52) U.S. Cl.
  CPC ......... *C12Q 1/6806* (2013.01); *C12Q 1/6855* (2013.01); *C12Q 1/6869* (2013.01)

(58) Field of Classification Search
  None
  See application file for complete search history.

(56) References Cited

U.S. PATENT DOCUMENTS

2013/0261027 A1* 10/2013 Li ................. C12Q 1/6806
    506/26

* cited by examiner

*Primary Examiner* — Angela M. Bertagna
(74) *Attorney, Agent, or Firm* — Richard Aron Osman

(57) ABSTRACT

The invention provides materials and methods to identify and analyze in a genome-wide manner the structural determinants of this organization. Next generation sequencing methods, combined with a novel assay and integrated data analysis, are used to map the long-range interactions in chromatin that are involved in the regulation of transcription.

4 Claims, 7 Drawing Sheets

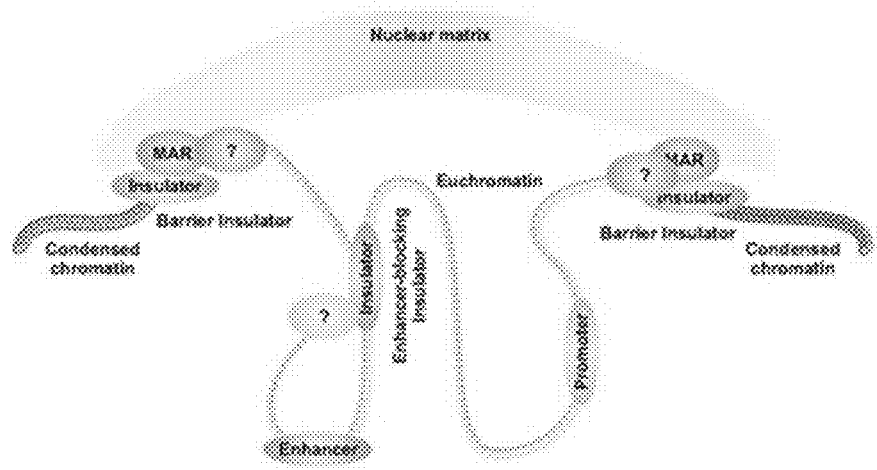
Fig. 1
Fig. 2A
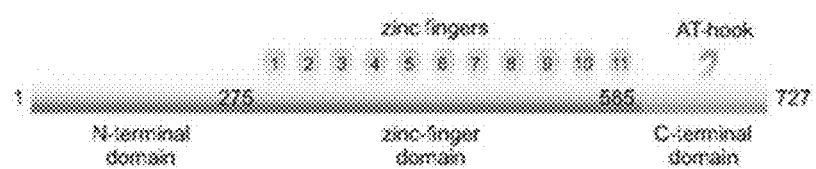
Fig. 2B
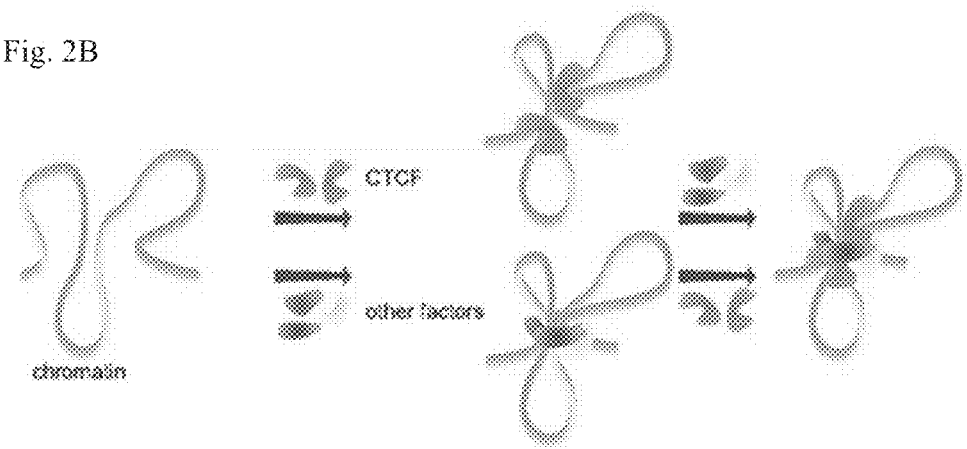

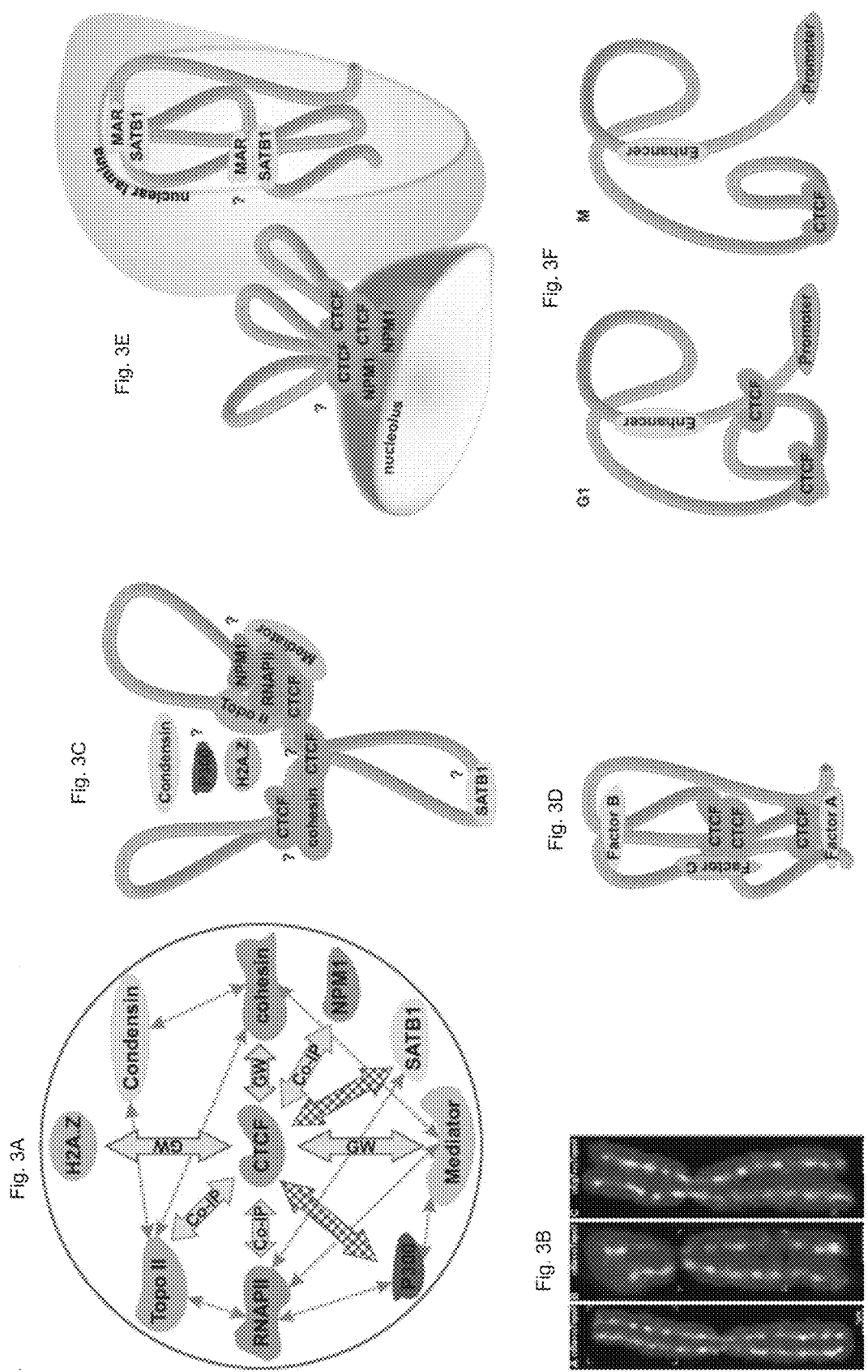

MAPPING CELL IDENTITY DETERMINANTS IN CHROMATIN

INTRODUCTION

Changes in chromatin organization are correlated with regulatory processes in health and disease ranging from embryonic stem cell differentiation to cancer, systemic lupus erythematosus, coronary heart disease, hypertension, diabetes, obesity, schizophrenia, Alzheimer's disease, and Parkinson's disease [1-2]. The invention provides materials and methods to identify and analyze in a genome-wide manner the structural determinants of this organization. Next generation sequencing methods, combined with novel assay and integrated data analysis, are used to map the long-range interactions in chromatin that are involved in the regulation of transcription.

SUMMARY OF THE INVENTION

The invention provides materials and methods for mapping contacts between different sectors and parts of chromatin with high-resolution, selectivity, efficiency and certainty. Chromatin structure defines cellular identity and may change dynamically in response to internal and external stimuli. Patterns of chromatin organization are different in healthy and diseased cells. The assay can be used to determine these patterns in various cells and tissues. Results of the assay can be correlated: with progression of disease or variability of outcomes resulting from a specific therapy, with the type or strength of stimuli used to modulate the pattern of contacts, or with patterns of contacts in other cells.

One innovation is the ligating of circularization and sequencing adapters in a one-step procedure, which increases the sensitivity and yield of productive circularization. The use of site-specific recombination (e.g. Cre-Lox)-based circularization and affinity (e.g. biotin)-labeling allows for efficient selection of properly ligated fragments, even from very diluted solutions. The reaction in diluted solution minimizes the level of artifacts. Additionally, presence of specific Cre-Lox sequences allows for running an additional sequencing reaction to confirm for every sequenced fragment that the circularization reaction had place.

Our method allows for mapping short-range contacts and this was previously impossible on genome-wide scale. It also has higher specificity and sensitivity. Many current assays for diagnosing or characterizing cellular states require a specific hypothesis about a factor or factors that participate in formation of these states, i.e. we test only things which we know about it and can very easily miss an important factor that contributes to observed phenomenon. Our assay fixes the problem. It enables testing and assaying states previously unavailable as it maps physical contacts between parts of the chromatin, and not necessarily mediators of the contacts, even though these mediators can be mapped or determined by applying modified versions of the assay.

There is no current technology that can achieve similar sensitivity, resolution and specificity. The 3C technology is not a genome-wide assay; the Hi-C method is low-resolution method and is not specific enough to provide information about short-contacts.

The invention may be used in multiple applications, including:
Diagnosis of epigenetically-driven disorders, e.g. cancer, cancer progression, loss of imprinting and others, by comparing the results of this assay between a sample from a patient and a reference sample (can be from the same patient if progress of disease or treatment is measured).

Testing how drugs and chemicals affect chromatin structure, which can be done in both directions i.e. testing drug efficacy by analyzing contacts in drug-treated cells, testing drug toxicity or side-effects by analyzing contacts in drug-treated cells, animals or human subjects, testing if a particular chemical substance is safe and non-toxic, and so on.

Quality control in regenerative medicine. For instance, artificially grown tissues and stem cell products can be dangerous and unpredictable because the source cells are induced to temporarily lose their chromatin- or environment-based identities and it is unclear how close the resulting tissues/cells mimic healthy tissues/cells. Our assay can compare maps of contacts in such therapeutic cells to "standard/target" cells and measure their similarities and differences. Additionally, one can confine examination to a particular specific signature of only a selected or correlated group of contacts defining cells, so the analysis does not have to be genome-wide.

In one embodiment the invention provides a method for processing DNA fragments, comprising by ligating in a single reaction dN-tailed, blunt-end, cross-linked DNA fragments to four duplex adapters: R1 and R2 recombination adapters and S1 and S2 sequencing adapters, wherein the recombination adapters each contain a site-specific recombinase target site and R1 contains an affinity tag.

The method may further comprise one or more subsequent steps of: (a) recombining the target sites with a corresponding site-specific recombinase; (b) isolating recombined fragments comprising the affinity tag; (c) amplifying by PCR the recombined fragments with primers complementary to the sequencing adapters; and (d) sequencing the amplified PCR product.

The method may further comprise one or more antecedent steps of: (i) fragmenting cross-linked chromatin into 300-600 bp fragments; and (ii) blunt end and dN tailing the fragments.

In combination, these steps provide a method of isolating consecutively connected fragments that contain genome parts interacting at long distances.

R1 and R2 are recombination or circularization adapters. They contain a sequence for recombination, such as Cre-Lox, either symmetrized or not (CreLoxP site, 13-8-13 bp). Other site-specific recombination systems may be used, such as FLP-FRT, PhiC31, VCre/VloxP and SCre/SloxP (Suzuki et al. Nucl. Acids Res., 2011, doi: 10.1093/nar/gkq1280), etc. R1/R2 could be Y-adapters or not. S1 and S2 are sequencing adapters. These can be any type of standard Illumina adapters (Y adapters), and they can also be non-Illumina adapters. They are used for the PCR selection after recombination. For some reactions, such as targeting very long pieces, one can use adapters not related to Illumina adapters and then follow it with a second fragmentation and ligation of Illumina adapters.

In particular embodiments during ligation we add adapters for ligation in equal ratios i.e. S1:S2:R1:R2 should be essentially 1:1:1:1, and/or as close to 1:1:1:1 as practical. Then we perform ligation, wherein a piece of DNA/chromatin with four ends generates the following possibilities (assuming for this illustration that S1=S2=S and R1=R2=R): end1:end2:end3:end4, and then all combinations are variations on the following:
S:S:S:S
S:S:S:R
S:S:R:R (productive—half of them will give us product of interest after circularization)
S:R:R:R
R:R:R:R An example of two oligonucleotides that we used for some experiments:

CPRIT-1S:
/5'Phos/ct(biot)gctg-CreLoxP site-atgcca t(cy5)t

CPRIT-2S:
5' aatggcat-CreLoxP site-cagcag* T 3'

After annealing they create duplexes ready for ligation from the/5'Phos/ct(biot) side.

A label or tag like the Cy5 is optional. It cleans the reaction, but we can also loose material during purification or cleaning, so it is no always justified. In any event, any affinity label can be used as long as it is different from the second label (e.g. biotin). Cy5 is convenient because of readily available antibodies, and it gives fluorescence which makes it easy to quantify the outcomes.

An affinity tag, such as biotin, is required for selection, though any other strong binders can be used, including having the oligos with a binder like digoxigenin or EdU introduced during synthesis, which can then be followed by CLICK-based selection or with a special base as isoC and then use isoG derivatized beads/oligos to select. Biotin-mediated interactions is strong and relatively inexpensive.

An important and independent improvement is ligating all adapters—the ones for circularization called R1/R2 and the ones for sequencing S1/S2—in one reaction. Also R1 may be the same as, or different than R2, and S1 maybe the same as, or different than S2. This increases sensitivity of the assay significantly over any existing solutions. The assay allows mapping relatively short-range contacts (high-resolution), which was before impossible.

Cross-linking of DNA-DNA or protein-DNA is often done by formaldehyde, but there are other methods, which can be used, including in cell lines or even living organisms. For example, our methods can use 5-ethynyl-2'-deoxyuridine (EdU), EU and derivative (2S)-2-deoxy-2-fluoro-5-ethynyluridine (F-ara-EdU), which all generate very specific substitutions in DNA with relatively high frequency. These derivatives have the ethynyl group that facilitates CLICK chemistry. We can use DNA/Chromatin labeled with EdU, EU and F-ara-EdU and add PEG-based multivalent linkers of different length containing 2-4 arms with azide groups at the ends. This allows mapping contacts at different length scales, wherein PEG-based linkers work as rulers and multiple arms allow one to reconstruct higher-order structural patterns. Our use of PEG-based linkers as rulers is also separately inventive. They are commercially available and can be readily synthesized, and were introduced to modify chemically various surfaces rather than to be used in the context of mapping contacts in DNA.

The invention includes all combinations of recited particular embodiments as if each combination had been laboriously recited.

BRIEF DESCRIPTION OF THE DRAWINGS

FIG. 1. Two types of insulators: barrier insulators preventing spreading of the condensed chromatin and enhancer-blocking insulators preventing functional interactions between promoters and enhancers. A schematic view of chromosomal loops anchored at nuclear matrix elements for barrier insulators and chromosomal loops for enhancer-blocking insulators.

FIG. 2. Schematic representations of: (A) CTCF; (B) two hypotheses regarding possible ways of hierarchy in process of chromatin organization by CTCF: CTCF molecules bind first, generating structures that allow for binding of other macromolecules (top); other macromolecules bind first, generating structures that provide a platform for CTCF molecules binding (bottom).

FIG. 3. A. Associations between proteins to be tested. Proteins selected for mapping contacts and their associations with CTCF and each other. GW labels genome-wide mapping of associations, Co-IP—co-immunoprecipitation, blue arrows label anti-correlations revealed in some experiments; B. Anti-correlated pattern of immunostaining for topoisomerase II and condensing. The copy of FIG. 5 A-C from work by K. Maeshima and U. K. Laemmli [22] representing patterns of staining with antibodies against topoisomerase II (green) and two subunits of condensin (red): Smc3 (A, B) and Eg7 (C) in mitotic chromosomes; C. How are the loops defined? D. How are different types of loops oriented in respect to each other? E. How do different loops cluster? F. How do different loops change across the cell cycle?

DETAILED DESCRIPTION OF PARTICULAR EMBODIMENTS

Figure 4A:
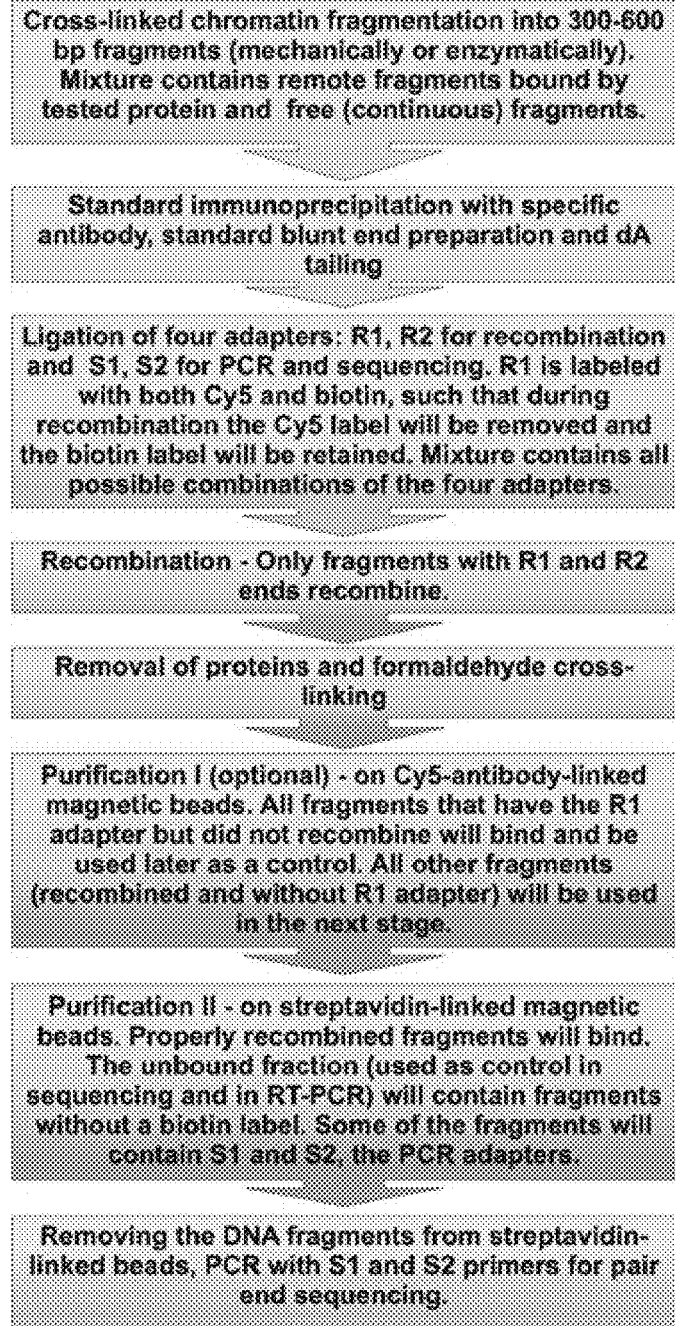
FIG. 4a and FIG. 4b. Flowchart view (FIG. 4a) and schematic view (FIG. 4b) of a novel assay targeting determination of long-distance interactions in chromatin. 51 and S2 represent Illumina's PCR primers that can be modified to allow multiplexing. R1=R2 for adapters modified with LoxS sequences.

We disclose a novel assay and its use in mapping long-range interactions in chromatin to establish the character of the long-range interactions and to identify markers of cancer. The invention allows us to map chromatin contacts by combining massive parallel sequencing with a biochemical approach derived from novel insights regarding the nature of how DNA structure organizes chromatin, that: (1) the topology of DNA contributes to the long-distance interactions in eukaryotic chromatin, and (2) the map of topologically-defined and other types of long-distance interactions correlates with the accumulated body of genome-wide epigenetic signatures in cells. The invention provides a new type of epigenetic signature combined with a robust method of its determination, and defines new markers to be used in research and diagnosis.

Long-distance interactions in chromatin remain an enigma in cellular biology (2). Not only cell fate control (3-11), but also chromatin territories and mitotic cell division, require thousands of specific contacts per chromosome between segments that may be distal in sequence by up to 1-2 millions base pairs. The problem of how these contacts are created and maintained is still unsolved. Based on many lines of evidence analyzed over the years, including an earlier proposal in this area (12), my lab has proposed that the most plausible mechanism involves, among other structures (13-14), a particular-type of DNA-DNA interaction, called hemicatenane. In our model, the (re)-positioning of these structures is controlled by remodeling complexes, which are both guided by histone modifications and also able to form them. Hemicatenanes are known to be involved in DNA replication (15) and other aspects of high order DNA structure (12, 16). Additionally, they have a very high affinity to cancer-related regulators, e.g. p53 (17) and HMGB1 (18-19). Hemi-catenated structures are defined by an intertwined DNA topology, and so they would be preserved even after having stripped DNA of proteins. The idea that cell identity can be identified and described by its structural signature encoded in the DNA topology is entirely novel. Confirming that both healthy and malignant cells have specific, structural signatures that are identifiable in naked genomic DNA by sequencing would have an immediate impact on cancer research, resulting in a novel method for characterizing epigenetic features specific to a particular cancer type and, in perspective, allowing for more effective, personalized approaches to treatment.

The related approaches of mapping contact interactions in chromatin are: Chromatin Interaction Analysis using Paired-End Tag sequencing (ChIA-PET) (20-21) and Hi-C (22-23). However, both techniques have significant limitations. In previous cases there was no inherent assay specificity towards interacting fragments (as opposed to self-ligated fragments), so protocols were necessarily adjusted to increase signal. With ChIA-PET it was achieved by chromatin immunoprecipitation, which may not be used to isolate the interaction structures we are postulating. With Hi-C, the signal was increased by extensive cross-linking combined with cutting DNA kilobases apart using six-position specific restriction enzymes. This resulted in the selection (and so, averaging) of mostly non-specific contacts, and consequently poor mapping resolution, reported only at 1 Mbp (23). In contrast we can obtain a cellular identity signature with even finer resolution than 2 kb resolution in ChIA-PET and to map only permanent contacts, without those accidentally trapped by cross-linking.

The invention provides genome-wide mapping of long-range contacts in chromatin isolated from human cell lines and identifying therefrom epigenetic signatures. That specialized, non-B-DNA structures contribute to long-distance interactions is demonstrated using a novel assay with high selectivity towards structures participating in long-distance contacts in chromatin. The output of this procedure is used for pair-end Illumina sequencing, which is followed by assignment of the paired reads to the genome assembly and analysis of statistical significance of the mapped contacts. Then we discern differences between maps describing long-distance interactions in selected cell lines, and use cell lines, such as GM12878, K562 and HUVEC to correlate our data with genome-wide data accumulated by the ENCODE consortium.

To show that topologically restrained nucleic acid contributes to long-range interactions in eukaryotic chromatin we conceived a novel assay (FIG. 7), with high selectivity and built-in internal controls. The assay works well on both genomic DNA depleted of proteins and on more traditionally isolated chromatin, including immune-precipitated samples. We break genomic DNA isolated from HeLa cultures into 300-600 bp fragments. This size is sufficiently long to allow for effective ligation within connected structures (20, 24) (FIG. 7) and sufficiently short, so that a ligated pair could be identified directly by Illumina pair-end sequencing (25). To prepare for the contact-specific ligation, fragmented DNA is first ligated with four different duplex adapter sequences supplied together, with one of the adapters containing a biotinylated nucleotide. In the next step, two of the adapters are ligated through highly specific Cre-lox recombination. This results in two possible structures: (1) consecutively connected fragments that contain genome parts interacting at long distances (our desired signal) or (2) topologically-locked fragments (FIG. 7) that provide additional signal characterization/control. A two tier selection process follows: (1) purification of the mixture with streptavidin-linked magnetic beads, wherein the unbound fraction is washed away to be used as an additional control; and (2) PCR with primers complementary to the other two adapters. The PCR output needs only to be size selected and quantified to be loaded onto the sequencing lane of the Illumina platform to produce 10-20 million paired-end reads. All our steps combined, are no more complex than Roche paired-end genomic sequencing procedure. This mate-pair procedure provides a point of reference for our experimental protocol, since in both cases the sequenced insert has to go through similar steps: Cre-lox recombination, biotin purification, and four ligations with similar set of adapters. A significant advantage of our experimental approach is its selection for the presence of more than two adapters in the joined DNA segments. This eliminates unconnected fragments, which are expected to numerically dominate results of genomic fragmentation in the absence of crosslinking.

Hemicatenates in chromatin may have a more complex structure, such as interacting pairs of D-loop or G-quadruplex/I-site structures (26). Such complex structures would be positionally stable until re-ordered by specific nuclear machinery. Once the hemicatenate is extended by 20 or more bp of DNA duplexes on each of the four ends, the structure should be biochemically stable. Since the sonication process is less well understood in terms of the forces and intermediates involved, we can obtain the putative connected DNA fragments also by endonuclease-based approaches.

Figure 7A:
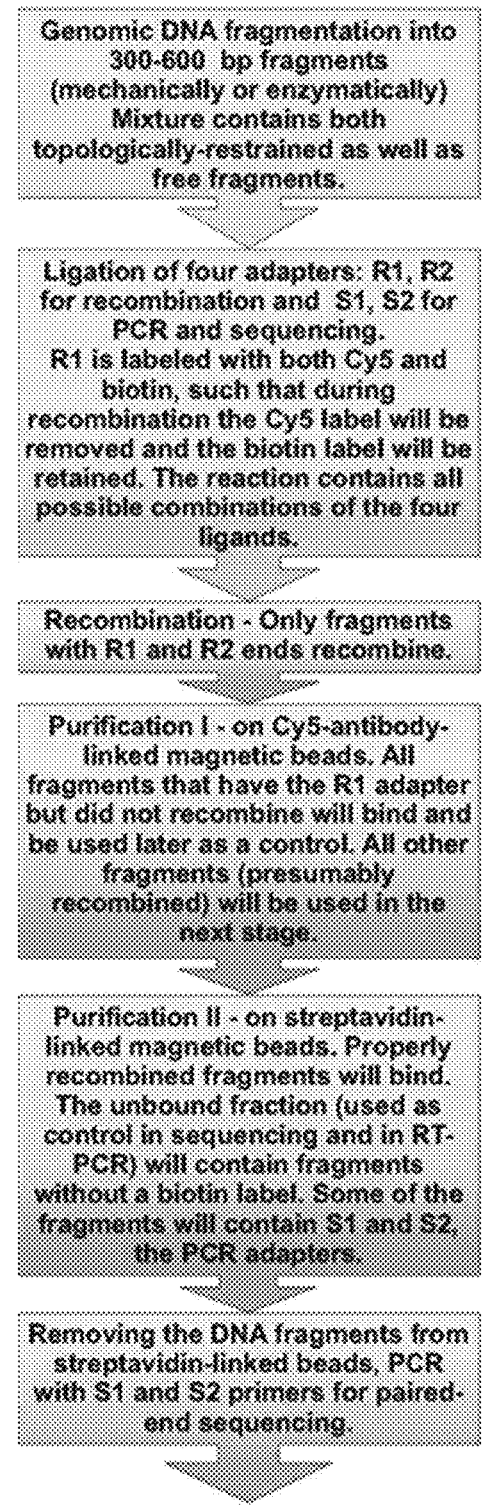
FIG. 7a and FIG. 7b. Flowchart view (FIG. 7a) and schematic representation (FIG. 7b) of novel assay targeted towards topologically defined signatures in genomic DNA resulting from controlled fragmentation of chromatin.
Figure 7B:
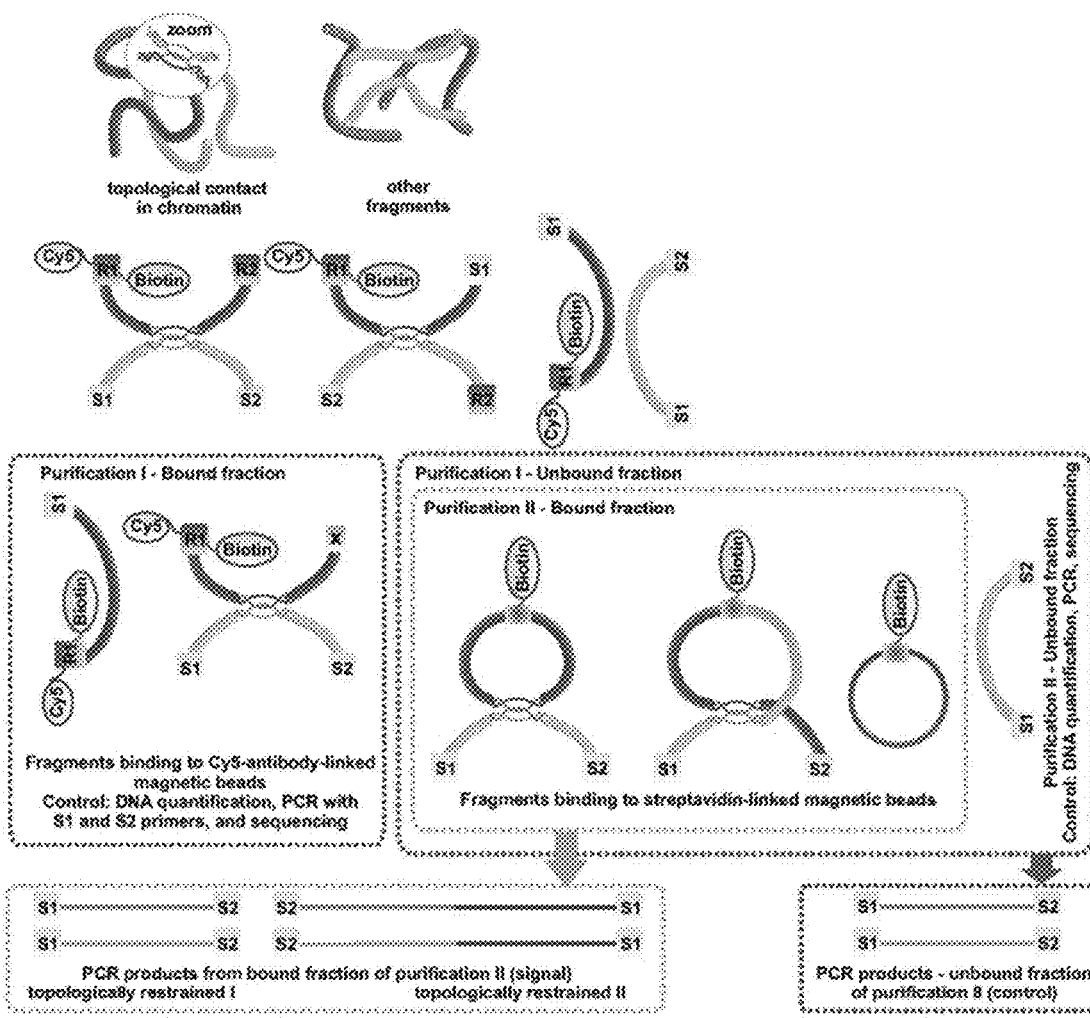

The products containing topologically linked but not covalently connected fragments (FIG. 7) are sensitive to various procedures: topoisomerases, a nicking nuclease-plus-ligase substitute for topoisomerase I or simple denaturation with high temperatures. We account for the impact of these procedures to characterize the nature of topological connections and, at the same time, to optimize the protocol for contact mapping. We can also improve the contact-map signal by modifying the adapter with a biotin tag by adding a new, distinct tag, on the adapter's opposite end. Cre-lox recombination removes the DNA fragment with the second tag so that its presence indicates that recombination did not occur. Affinity purification for the second tag removes a source of reads not contributing to the chromatin contact map (FIG. 7). The control for specificity can be improved by adding phage λ DNA into the starting sample in the amount of 10% of the sample DNA. Sequencing can identify phage λ DNA without any ambiguity. After the first purification, phage λ DNA sequences can only originate from a lack of specificity (e.g. cross-recombination), so their quantification will define whether or not the protocol needs to be adjusted.

We can also analyze cell cycle progression. To obtain S-phase cells we synchronize them with the double thymidine block. The release from this block, after completion of replication, produces G2-phase cells and the addition of nocodazole after produces predominantly M-phase cells.

We can also map contacts in specifically perturbed chromatin. In particular, past research indicates a bio-chemically stable core chromosomal structure (scaffold or skeleton) present after removal of all histones in mitotic chromosomes (1, 27-30). We can synchronize mitotic cells and prepare these skeletal structures, then gently digest them with nucleases, as to employ the same contact-mapping procedure defined earlier. We can also check if interphase cells have the same contact map or not. We can also compare the starting cell line with additional ones: K562, GM12878, and HUVEC, one cancerous and two normal, cell lines from the mesodermal lineage.

Data Analysis: Illumina output is analyzed through the standard manufacturer's software to identify clusters and assignment of their sequences, followed by mapping to the human genome assembly. Paired-end reads can map close to each other in the genome, classifying them as coming from a single fragment. The alternative—being mapped far away—makes the pair a candidate for defining a chromatin contact. Before being accepted as such, the pairs pass two tests: in the first we use stringent criteria to define that both reads in the pair are unambiguously genome-mapped, and in the second we check if the pair does not originate from a structural variation in the studied cell line. We use 36 bp long reads during assay development to reduce cost and 75 bp long reads after optimization to increase the number of unambiguously mapped reads. To facilitate rejection of false positives, we use a library of mostly unmapped sequences that have multiple copies in the genome, but are similar (no more than one position is different) to fragments uniquely present in the human genome assembly. The number of false positives resulting from structural variations is estimated from sequencing the first wash (FIG. 7). We can also perform a mate-pair sequence run on our chosen cell-lines to create a database that will screen for a signal arising from structural variations. There are a number of internal controls built into the analysis. Functional contacts in the genome come predominantly within the range of about 2 Mbp, as observed in cis-regulated processes and ChIA-PET (20). Non-specific contacts and artifacts are more randomly distributed as they can spread over a whole genome volume, 700 times larger than the cis-regulation range.

The sequencing results generally contain two populations corresponding to two possible outcomes of the recombination reaction (FIG. 7). The peak positions of the topologically-locked fragments (arising from short continuous fragments of the genome) should agree with the one dimensional projection of the contact map for the second population, which is derived from the ligation of fragments separated in sequence. The signal correlation between these two populations provides a measure of the assay's biochemical robustness. The measure of depletion of fragments in the wash defines how much initial sample preparation and in vivo reproducibility contributes to the robustness of the approach.

The next level of the analysis is the correlation of the signal with known genome-wide properties, which can include a search for sequence signatures using available standard tools (31), and/or correlating the signal with publicly available results. For example, just testing for correlation with more than a 1000 ENCODE tracts downloaded from the UCSG genome browser site can be informative and accomplished with relatively little effort. Significant correlations can be established even with a relatively weak signal by averaging over many sites in the genome, typically in the range of 10,000-100,000 sites for various epigenetic markers. We can also identify correlations with cohesin binding sites, transcription factor binding sites, CpG islands or evolutionary conservation, and can analyze differences between our data from different cell lines with a mixture model and will correlate these differences with differences in the ENCODE data tracks involving the same cell lines.

REFERENCES

1. Mullinger, A. M., and Johnson, R. T. (1980) Packing DNA into chromosomes, J Cell Sci 46, 61-86.
2. Belmont, A. S. (2006) Mitotic chromosome structure and condensation, Curr Opin Cell Biol 18, 632-638.
3. Dillon, N. (2006) Gene regulation and large-scale chromatin organization in the nucleus, Chromosome Res 14, 117-126.
4. Miele, A., and Dekker, J. (2008) Long-range chromosomal interactions and gene regulation, Mol Biosyst 4, 1046-1057.
5. Vernimmen, D., De Gobbi, M., Sloane-Stanley, J. A., Wood, W. G., and Higgs, D. R. (2007) Long-range chromosomal interactions regulate the timing of the transition between poised and active gene expression, Embo J 26, 2041-2051.
6. Sawan, C., Vaissiere, T., Murr, R., and Herceg, Z. (2008) Epigenetic drivers and genetic passengers on the road to cancer, Mutat Res-Fund Mol M 642, 1-13.
7. He, S. H., Dunn, K. L., Espino, P. S., Drobic, B., Li, L., Yu, J., Sun, J. M., Chen, H. Y., Pritchard, S., and Davie, J. R. (2008) Chromatin organization and nuclear microenvironments in cancer cells, J Cell Biochem 104, 2004-2015.
8. Galande, S. (2002) Chromatin (dis)organization and cancer: BUR-binding proteins as biomarkers for cancer, Curr Cancer Drug Targets 2, 157-190.
9. Rodenhiser, D. I., Andrews, J., Kennette, W., Sadikovic, B., Mendlowitz, A., Tuck, A. B., and Chambers, A. F. (2008) Epigenetic mapping and functional analysis in a breast cancer metastasis model using whole-genome promoter tiling microarrays, Breast Cancer Res 10, R62.
10. Chan, T. A., Glockner, S., Yi, J. M., Chen, W., Van Neste, L., Cope, L., Herman, J. G., Velculescu, V., Schuebel, K. E., Ahuja, N., and Baylin, S. B. (2008) Convergence of mutation and epigenetic alterations identifies common genes in cancer that predict for poor prognosis, PLoS Med 5, e114.
11. Rodenhiser, D. I. (2009) Epigenetic contributions to cancer metastasis, Clin Exp Metastasis 26, 5-18.
12. Gaillard, C., and Strauss, F. (2006) DNA topology and genome organization in higher eukaryotes: A model, J Theor Biol 243, 604-607.
13. Borek, D., and Otwinowski, Z. (2009) Topology of Eukaryotic Chromatin, J Biomol Struct Dyn 26, 913-913.
14. Borek, D., Otwinowski, Z. (2008) Kinetic control of eukaryotic chromatin structure by recursive topological restraints., Available from Nature Precedings < . . . hdl.handle.net/10101/npre.2008.2672.1>.
15. Lucas, I., and Hyrien, O. (2000) Hemicatenanes form upon inhibition of DNA replication, Nucleic Acids Res 28, 2187-2193.

16. Pohjoismaki, J. L., Goffart, S., Tyynismaa, H., Willcox, S., Ide, T., Kang, D., Suomalainen, A., Karhunen, P. J., Griffith, J. D., Holt, I. J., and Jacobs, H. T. (2009) Human heart mitochondrial DNA is organized in complex catenated networks containing abundant four-way junctions and replication forks, J Biol Chem 284, 21446-21457.
17. Stros, M., Muselikova-Polanska, E., Pospisilova, S., and Strauss, F. (2004) High-affinity binding of tumor-suppressor protein p53 and HMGB1 to hemicatenated DNA loops, Biochemistry-Us 43, 7215-7225.
18. Jaouen, S., de Koning, L., Gaillard, C., Muselikova-Polanska, E., Stros, M., and Strauss, F. (2005) Determinants of specific binding of HMGB1 protein to hemicatenated DNA loops, J Mol Biol 353, 822-837.
19. Gaillard, C., Borde, C., Gozlan, J., Marechal, V., and Strauss, F. (2008) A high-sensitivity method for detection and measurement of HMGB1 protein concentration by high-affinity binding to DNA hemicatenanes, Plos One 3, e2855.
20. Fullwood, M. J., Liu, M. H., Pan, Y. F., Liu, J., Xu, H., Mohamed, Y. B., Orlov, Y. L., Velkov, S., Ho, A., Mei, P. H., Chew, E. G., Huang, P. Y., Welboren, W. J., Han, Y., Ooi, H. S., Ariyaratne, P. N., Vega, V. B., Luo, Y., Tan, P. Y., Choy, P. Y., Wansa, K. D., Zhao, B., Lim, K. S., Leow, S. C., Yow, J. S., Joseph, R., Li, H., Desai, K. V., Thomsen, J. S., Lee, Y. K., Karuturi, R. K., Herve, T., Bourque, G., Stunnenberg, H. G., Ruan, X., Cacheux-Rataboul, V., Sung, W. K., Liu, E. T., Wei, C. L., Cheung, E., and Ruan, Y. (2009) An oestrogen-receptor-alpha-bound human chromatin interactome, Nature 462, 58-64.
21. Fullwood, M. J., Han, Y., Wei, C. L., Ruan, X., and Ruan, Y. (2010) Chromatin interaction analysis using paired-end tag sequencing, Curr Protoc Mol Biol Chapter 21, Unit 21 15 21-25.
22. van Berkum, N. L., Lieberman-Aiden, E., Williams, L., Imakaev, M., Gnirke, A., Mirny, L. A., Dekker, J., and Lander, E. S. (2010) Hi-C: a method to study the three-dimensional architecture of genomes, J Vis Exp.
23. Lieberman-Aiden, E., van Berkum, N. L., Williams, L., Imakaev, M., Ragoczy, T., Telling, A., Amit, I., Lajoie, B. R., Sabo, P. J., Dorschner, M. O., Sandstrom, R., Bernstein, B., Bender, M. A., Groudine, M., Gnirke, A., Stamatoyannopoulos, J., Mirny, L. A., Lander, E. S., and Dekker, J. (2009) Comprehensive mapping of long-range interactions reveals folding principles of the human genome, Science 326, 289-293.
24. Hoess, R., Wierzbicki, A., and Abremski, K. (1985) Formation of small circular DNA molecules via an in vitro site-specific recombination system, Gene 40, 325-329.
25. Harismendy, O., and Frazer, K. (2009) Method for improving sequence coverage uniformity of targeted genomic intervals amplified by LR-PCR using Illumina GA sequencing-by-synthesis technology, Biotechniques 46, 229-231.
26. Huppert, J. L., and Balasubramanian, S. (2007) G-quadruplexes in promoters throughout the human genome, Nucleic Acids Res 35, 406-413.
27. Laemmli, U. K., Cheng, S. M., Adolph, K. W., Paulson, J. R., Brown, J. A., and Baumbach, W. R. (1978) Metaphase chromosome structure: the role of nonhistone proteins, Cold Spring Harb Symp Quant Biol 42 Pt 1, 351-360.
28. Paulson, J. R., and Laemmli, U. K. (1977) The structure of histone-depleted metaphase chromosomes, Cell 12, 817-828.
29. Adolphs, K. W., Cheng, S. M., Paulson, J. R., and Laemmli, U. K. (1977) Isolation of a protein scaffold from mitotic HeLa cell chromosomes, Proc Natl Acad Sci USA 74, 4937-4941.
30. Mullinger, A. M., and Johnson, R. T. (1979) The organization of supercoiled DNA from human chromosomes, J Cell Sci 38, 369-389.
31. Pepke, S., Wold, B., and Mortazavi, A. (2009) Computation for ChIP-seq and RNA-seq studies, Nat Methods 6, S22-32.

EXAMPLES

The disclosed technology can resolve how specificity in chromatin contacts is achieved both in transcriptional control and in mitotic organization. A particular application is how enhancers, distal to the start of transcription, can influence it by acting in cis, and how insulators can be enhancer-blocking or can form the barrier to heterochromatin spread (barrier insulators) [FIG. 1].

The importance of chromatin organization problem was recognized and studied in several cellular contexts for selected loci, e.g. MYC [3], H19/insulin-like growth factor (Igf2) [4], β-globin [5], human major histocompatibility complex class II (MHC-II) [6], where researchers tried to determine chromatin contacts' characteristics and the rules behind their specificity (reviewed in [7-8]).

CCCTC-binding factor (CTCF)—a "master weaver of chromatin structure" [7]—binds in a sequence-dependent manner at tens of thousands of sites in the human genome [9-12] and has a confirmed role in transcription activation and silencing, enhancer blocking and/or barrier insulation and genomic imprinting. CTCF has a number of favorable properties making it particularly suitable to create reference contact map for subsequent analyses. It is one of the few known proteins in the human genome that binds to evolutionary conserved sites with a unique, highly-informative (rarely encountered by chance) sequence motif [9] [FIG. 2]. Most of the observed binding sites have only one instance of this motif, indicating that only one copy of the protein binds there. In multiple, one-dimensional chromatin immunoprecipitation followed by sequencing (ChIP-seq) studies, CTCF peaks were consistently one of the highest observed by this technique [11, 13-14]. There is an increasing acceptance that all the regulatory functions of CTCF derive from its role in defining long-range chromatin interactions [7-8]. In genome-wide experiments, specific subsets of CTCF-binding sites were overlapping with subgroups of binding sites for cohesin [15-16], RNA polymerase II [17] and histone variant H2A.Z [11]. Cohesin is known to be involved in chromatin condensation and sister chromatids cohesion, while also in DNA repair and in transcription. RNA polymerase II is a marker of transcription and histone H2A.Z marks heterochromatin with preferential localization at the boundaries with euchromatin. Correlative analysis of contact maps for all the above proteins in two cell cycle stages allows for the separation and grouping of various functions. Co-localization of H2A.Z and CTCF in genome coordinates identifies barrier insulator sites, whereas contact maps shows whether specific patterns exist differentiating barrier-type insulators from others.

Patterns in one- and two-dimensional contact maps also reveal how CTCF-binding sites in introns are compatible with transcription and whether they have spatial properties differentiating them from other CTCF sites, e.g. low occupancy or lack of loops emanating from such sites. In addition, the role of insulation in transcriptional regulation can be revealed by correlating CTCF-contact maps with cohesin, and also with two transcription-related factors p300 (called also E1A binding protein p300) [18-19] and Mediator subunits (Med1 and Med12) [10, 20]. p300 binds to enhancers, whereas Mediator is localized on the other end of the enhancer-mediated loop. Hence our methods can determine whether insulation requires just the presence of CTCF or also of cohesin and/or chromatin loop emanating from such sites [reviewed in [21]].

We selected chromatin in the GM12878 cell line G1 phase and metaphase to identify contacts specific for active transcription (G1), absent in mitotic state, in which transcription is suspended. On the other hand, contacts specific to mitosis can transform chromatin into structurally highly organized state. The similarities between G1 and metaphase provide information about general rules of chromatin organization and the persistence of specific contacts in cell division, resolving epigenetic mechanisms.

Two architectural proteins of mitotic chromosomes: topoisomerase II and condensing, were also selected for analysis Immunostaining has revealed a "barbed-wire" pattern of topoisomerase II and condensin localizations being anti-correlated in mitotic chromosomes [FIG. 3]. These two proteins have been postulated to organize a so-called chromosomal scaffold, and the question of how these two proteins can specifically organize a structure so large as to be visible under microscope, can be resolved by contact maps for both topoisomerase II and condensin in two different stages of cell cycle.

Matrix Attachment Elements (MARs) and Scaffold Attachment Elements (SARs) have been discussed as chromatin loop organizers with respect to nuclear envelope and in the regulation of transcription. The role of nuclear matrix in transcription, insulation and condensation important can be resolved by mapping two-dimensional contacts and binding sites for SATB1 (special AT-rich sequence-binding protein-1)—a transcriptional factor and an established marker of MARs [reviewed in [23]]. The contact mapping approach can even address the issue of nucleolus as a potential structural organizer, if a significant number of contacts for the tested proteins map to one of multiple copies of DNA encoding ribosome—a mark of nucleolus. CTCF has already been implicated by immunostaining to have preferential co-localization with nucleolus [24]. The additional target is nucleophosmin (nucleolar phosphoprotein B23, numatrin, NPM1) that associates with CTCF, with nucleolus and surface of mitotic chromosomes [25] [FIG. 3].

Additional biological information comes from correlating contact maps with various sequence properties and with experimental genome-wide data collected by ENCODE ( . . . www.genome.gov/10005107), and in correlating such maps with DNA methylation data, specific histone modifications, DNA hypersensitivity sites and presence of other, already mapped transcription factors. The availability of this data prompted the choice of the GM12878 cell line—it is a commercially available, lymphoblastoid cell line used both by the ENCODE and HapMap projects, characterized by a relatively normal karyotype and robust growth. Integration of two-dimensional maps for protein proposed here with one-dimensional information can be used to assemble a three-dimensional reconstruction of the nucleus functional architecture.

In ChIP-seq studies, the standard control is the input chromatin—sheared and processed according to the same protocol, but without a specific antibody. We can use the same approach to controls in generating contact maps. However, the input provides not only control and correction for data from the immunoprecipitated sample, but also contains relevant biological information worth of analyzing. The "input" contact map defines density distribution of, mostly non-specific, contact lengths across the genome. Analysis of such global distribution has been the subject of a Hi-C study [26], which used such a sample and identified regions of heterochromatin and euchromatin. The differences between input samples from G1 and M chromatin can help resolve the mechanism of chromosomal condensation. Additional analyses determine whether the contact map is specific to a particular protein or resembles the generic (input-like) map of contacts, after the correction for sequence preferences.

Experimental methods targeting genome-wide chromatin contacts include Chromatin Interaction Analysis by Paired-End Tag Sequencing (ChIA-PET), so far used only in the context of estrogen-receptor mediated contacts [27]. The number of reads defining specific contacts was a very small fraction (less than 1%) of all read sequences. Part of the problem was lack of selection against self-circularization, which reduced efficiency and created a highly elevated background for short contacts (50% false positives at 5 kbp distance between interacting fragments). Since the assay did not directly restrict the distance between the fragment sequenced and the actual contact, the authors reduced the resolution of the contact map to about 2 kbp, and were unable to analyze finer spatial structure. Additionally, there was no correction for input data. Another method for mapping contacts is Hi-C [26]. It has different, but serious shortcomings, making it unsuitable for most of my goals. The Hi-C method is based on using a sparsely-cutting, 6 bp-specific restriction enzyme, inherently reducing the resolution to a few thousands of bp. Cross-linking is necessary for all immunoprecipitation-based methods and was also used in Hi-C. With so few cuts by 6 bp cutters and no sonication, chromatin forms fragments too large for meaningful immunoprecipitation. Therefore, the Hi-C method as published is only suitable for low resolution, very long range contact mapping. Additionally, the limitation of computational analysis in Hi-C method reduced resolution even farther, to 1 Mbp. A third method [28], is similar to Hi-C in terms of mapping non-specific contacts using 6 bp cutters has more complex experimental protocol, but with similar resolution limitations and similar issues with respect to immunoprecipitation.

Figure 4B:
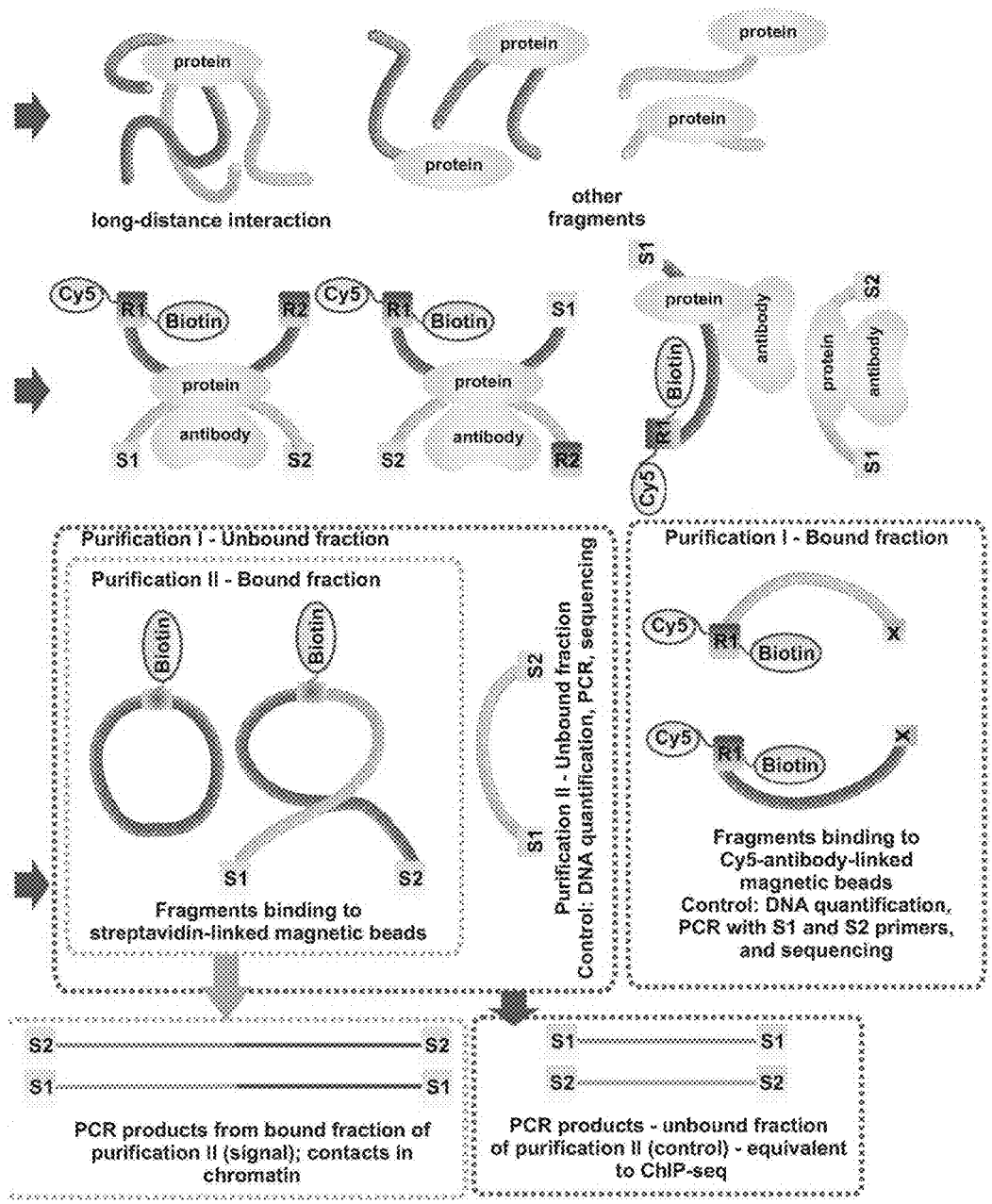

To generate maps of chromatin contacts we use synchronized GM12878 cell cultures. Synchronization enriches the signal, but it does not have to be perfect. For synchronization in mitosis we use nocodazole, which preserves the integrity of chromosomes better than colcemid. For synchronization in G1, serum starvation is used. In both cases, Fluorescence Activated Cell Sorting (FACS) is used to estimate the degree of synchronization, so an appropriate correction can be applied during data analysis. To isolate chromatin, we break cross-linked cells under mild conditions using digitonin rather than harsher detergents, and then follow standard protocols of chromatin immunoprecipitation with well-established commercially-available antibodies. Cross-linked chromatin is fragmented using sonication to about 300 bp fragments. This length is sufficiently long to allow effective ligation within connected structures [FIG. 4] and sufficiently short that a ligated pair can be identified directly by Illumina pair-end sequencing. At this point the procedure is modified according to a novel, highly-selective assay [FIG. 4] to obtain Illumina-ready libraries of DNA fragments. After standard preparation (polishing) of DNA ends in fragmented chromatin, they are ligated with two types of duplex adapter sequences supplied together. One type of adapters has the LoxS sequence (symmetrized version of LoxP) [29] containing a biotinylated nucleotide on one end and fluorescent label on the other. Other types of adapters correspond to either standard Illumina adapters or, in the case of multiplexing, to standard Illumina adapters extended by sequence tags [30]. After ligation, the chromatin sample is released from (protein G)-derivatized magnetic beads used for purification in all earlier steps and diluted to prepare for recombination. Dilution is used to prevent cross-ligation. Recombination between two LoxS ends is performed with Cre recombinase and release of fluorescently labeled fragments is used to monitor the efficiency of the process. In the next step we remove cross-linking and DNA-bound proteins. The resulting fragments contain, among others, two structures that can be sequenced: (1) consecutively connected fragments that contain genome parts interacting at long distances (our desired signal) and (2) short linear fragments equivalent to standard ChIP-seq signal [FIG. 4]. These shorts fragments do not have biotin labels and can be removed in the next step, where biotinylated fragments are isolated using streptavidin-coated magnetic beads. The presence of fluorescence in the wash defines the completeness of recombination and is used to optimize and quantify the efficiency of the assay. The fluorescent tag can be also used to deselect by IP fragments that do not contain proper adapters. Both the wash and the eluate from streptavidin-linked beads are used in PCR with standard sequencing primers to amplify the material prior to size selection, quantification and loading on Illumina sequencer. We use 80 bp or longer reads at each end to improve the completeness of the mapping, an additional improvement comparing to ChIA-PET. ChIA-PET, due to its experimental design, generates only 21 or 25 bp-long genomic location tags leading to significantly lower coverage. We have more than 85% coverage comparing to 58%, the limit of ChIA-PET.

One advantage of our approach is its selection for the presence of more than two adapters in the joined DNA segments. This eliminates unconnected fragments, which dominated the signal in the ChIA-PET experiment. Additionally, the probes used at different stages of the assay allow for its optimization and quantification, as they provide feedback as to the yield and efficiency at each step. For example, the question of how much sonication disrupts the complexes with chromatin contacts can be easily quantified here without sequencing, and the procedure can be modified to accommodate other strategies, e.g. non-specific nucleases like DFF40. High-affinity and efficiency of Cre recombinase, which does not require any other factors, allows for using very large dilutions to avoid reversing the reaction and cross-ligation between random chromatin fragments.

Figure 5:
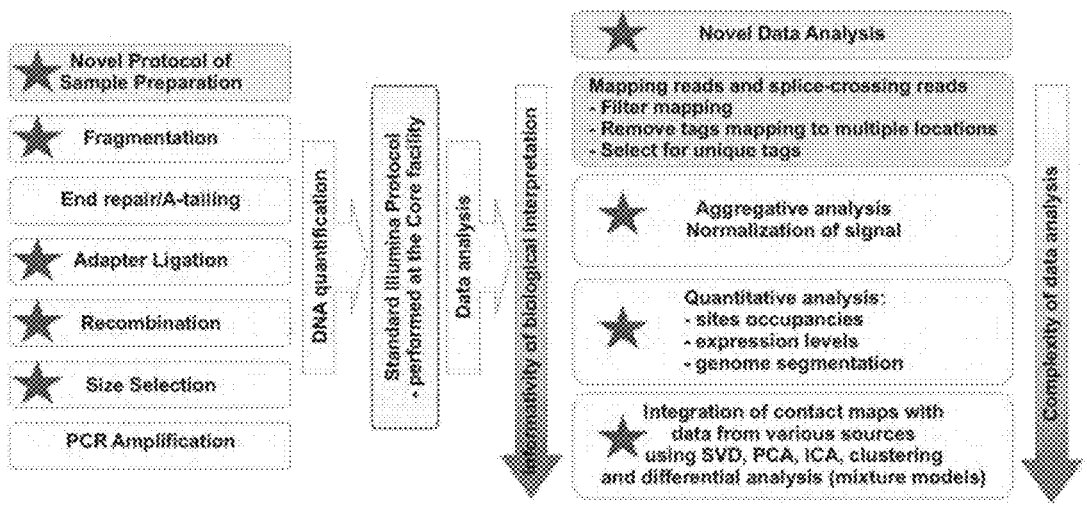
FIG. 5. A workflow for processing of a sample to generate a map of contacts followed by Illumina sequencing and custom data analysis. Red stars represent significantly improved or novel stages of sample and data processing. The novelty comes from using known and well-established procedures in new contexts.
Figure 6:
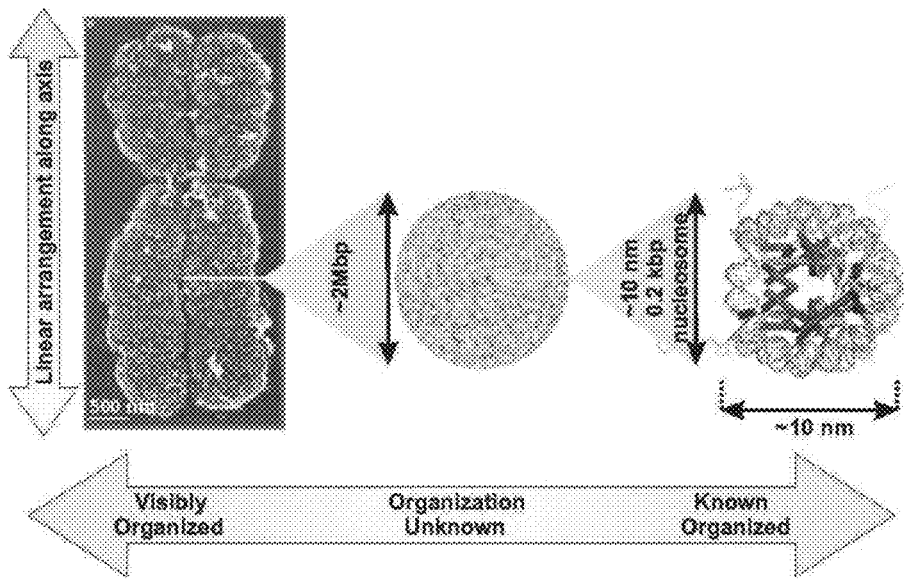
FIG. 6. Chromatin organization: on the left side, visibly organized, human chromosome 2 [34] with chromatid's diameter ~600 nm, representing ~2 Mbp of genomic DNA in the slice labeled on the figure; on the right, a structural model representing 0.2 kbp of genomic DNA with size 10 nm obtained from the crystal structure of a nucleosomal core particle; in the middle a cryo-electron microscopy section through chromatin showing lack of visible organization at the intermediate level.

Data from the sequencer enter a standard analysis pipeline [FIG. 5]: cluster identification, base calling and assignment of paired reads to a genome location. In the case of precisely repetitive sequences, e.g. telomeres, ribosomal RNA or alphoid repeats, each of them are considered as a single unit representing a genomic category. Paired reads in which one end corresponds to multiple genome locations are rejected from subsequent analysis as they are ambiguous in terms of contact location. The use of 80 bp reads minimizes the number of such rejects compared to the current ChIP-seq standard of 36-40 bp. To map specific contacts, the ChIA-PET tool program clusters contact pairs and displays their genomic distribution.

Massively parallel sequencing does not sample sequence space uniformly [e.g. [31]], and the number of reads is correlated with GC-content of the whole insert defined by paired-end sequenced fragments. Since the unsequenced part of the insert influences the bias, it is an indication of it originating from preparatory steps, e.g. PCR amplification, rather than sequencing itself. We employ the Poisson regression method of correcting for it, described in the context of RNA-seq [32], but easily adapted to ChIP-seq and contact mapping. The method was selected because of its sophistication in modeling bias for each read separately. It is important to correct for sequencing biases both for ChIP-seq and CCM-PET experiments. After such normalization for the effects of experimental factors, we can estimate the distribution of non-specific contacts in chromatin. This correction is important because, in contrary to input DNA used in ChIP-seq, where background reads should represent even distribution, we do not typically obtain a uniform 2-D distribution for contact maps' background; rather, most of the contacts will arise from non-specific interactions induced by local high density of chromatin. Most of non-specific contacts should be predominantly in a limited range, below 1 Mbp. As an initial approach, we calculate a distance-distribution function defined separately for euchromatin and heterochromatin regions, for which we expect different density of non-specific contacts. In the Hi-C method analysis, the authors reduced the resolution by binning very long-range interactions into 1 Mbp size segments. We can improve the analysis of non-specific background by employing Wiener-Fourier filtering methods, which provide the necessary resolution limit for signal estimation in an optimal fashion. The estimate of background of non-specific interactions cannot be simply subtracted from the contact map signal. It must be further corrected for the distribution of the studied protein within the genome. To achieve this we can use ChIP-seq data to obtain the profile of protein binding in genome coordinates, and apply this to both arguments (representing the contact pair) of the background function. Only after this operation can the contact map be analyzed in respect to the background map. The resulting magnitude of contact peaks represents the specificity of contacts. At this point, we can approach the questions with biological significance. First, we can ask if contacts mediated by the studied protein cluster in 3-D space, i.e. do they originate from particular foci? This question has never been approached by quantitative procedures in a genome-wide context and will require new computational methods. We can use here a singular value decomposition (SVD), already used in genomic data analysis in the context of linkage disequilibrium analysis [33]. Eigenvectors obtained from this analysis correspond to sets of genomic locations forming a focus (group) of consistent contacts. This analysis can address many questions regarding nuclear organization, e.g. it can analyze the concept of transcription factories and their organization. Each transcription factor may be related to a specific group of transcripts, or may exist due to spatial (3-D) optimization of the process that is independent on the type of transcript. The SVD analysis of RNA polymerase II-associated contacts and mediator-associated maps provide answers to this question. The CCM-PET assay provides an average over a population of cells. If transcription factors aggregate different transcripts in different cells, the contact map will be a very diffuse network, with SVD results dominated by a few large eigenvalues with very spread-out coefficients of eigenvectors. The opposite result indicates that transcription factors specifically group transcripts, with eigenvectors defining each group content.

The contact map for each protein can be used to determine if other factor-binding sites have strong influence on contacts, and different contact maps can be compared to each other, for example to see if contacts are allowed to penetrate each other, creating a more complex network of connections rather than loops emanating from the scaffold. Further information comes from the comparison between contact maps in mitosis and G1. The absence of transcription eliminates contacts present in transcriptional factories, reducing the number of very long range contacts. Analyses include data-driven approach-NMR-style, distance-restraint-based 3D reconstruction, and comparisons of various models of mitotic chromosome architecture to experimental data.

The assay and analysis have many more applications. For example, RNAi can be used to perturb the cellular state specifically and contact maps can be analyzed for the impact of such perturbations. Comparing the results for different types of cells is also a useful approach to study differentiation and epigenetics. Another extension of correlative analysis is to add information about factors involved in the definition of origins of replication. Comparative analysis of chromatin organization across species, particularly in model organisms, is another useful application. Holocentric chromosomes of C. elegans are more amenable than mammalian ones to the study of centromeric chromatin by sequence mapping.

This invention targets a new experimental direction in biology—high-resolution studies of contacts in chromatin, and between chromatin and other nuclear structures. It integrates three different and innovative aspects: a novel assay that combines high resolution, specificity and efficiency of mapping contacts; comparative studies of contacts associated with principal protein factors organizing chromatin and comparing different stages of the cell cycle, and quantitative correlative analysis. The assay employs two selective steps: biotin-streptavidin interaction and PCR with primers complementary to sequencing adapters.

Cross-linking and chromatin disruption methods, as in any ChIP protocol, can be optimized for each antibody, as they may have different affinity for targets and the complexes involved may differ structurally. For proteins that intrinsically and stably bind two DNA segments, an alternative to cross-linking can be pursued. This would require fast (less than 30 minutes) and efficient chromatin digestion (e.g. with DFF40 nuclease [35]), ligation and recombination before complexes assembled on chromatin are spontaneously dissociated.

Efficiency can be monitored by the quantification of DNA after biotin-streptavidin selection and by using RT-PCR with sequencing adapters. Only about 100 pg of unique sequence material (the one prior to amplification by PCR) needs to be produced to fill a sequencing lane that produces 30-40 million reads [37], out of which about a half is expected to satisfy the acceptance criteria—unique mapping in the genome and being clonally unique.

The integration of genomic-scale data describing interactions presents challenges [38], including the vast data space. Each human genome contact map potentially contains 1019 data points. To address adequate experimental sampling and computational limitations of algorithms the analysis can be performed in a data space of reduced size. Our methods take advantage of enrichment by immunoprecipitation to reduce the number of analyzed sites to associated loci. For inapplicable architectural proteins, we can use low-pass signal filtering, which is an improvement upon simple binning and a related approach of modeling distribution by sparse signal.

REFERENCES

[1] Zink, D. et al. Nat Rev Cancer, 2004. 4: 677-87. [2] Misteli, T., Cold Spring Harb Perspect Biol, 2010. 2: a000794. [3] Gombert, W. M. & A. Krumm, PLoS One, 2009. 4: e6109. [4] Ling, J. Q., et al., Science, 2006. 312: 269-72. [5] Splinter, E., et al., Genes Dev, 2006. 20: 2349-54. [6] Majumder, P. & J. M. Boss, Mol Cell Biol, 2010. 30: 4211-23. [7] Phillips, J. E. & V. G. Corces, Cell, 2009. 137: 1194-1211. [8] Gondor, A. & R. Ohlsson, Nature, 2009. 461: 212-7. [9] Xie, X., et al., Proc Natl Acad Sci USA, 2007. 104: 7145-50. [10] Kagey, M. H., et al., Mediator and cohesin connect gene expression and chromatin architecture. Nature, 2010. Advance publication on-line [11] Barski, A., et al., Cell, 2007. 129: 823-37. [12] Wendt, K. S., et al., Nature, 2008. 451: 796-801. [13] Kim, T H, et al., Cell, 2007. 128: 1231-1245. [14] Cuddapah, S., et al., Genome Res, 2009. 19: 24-32. [15] Schmidt, D., et al., Genome Res, 2010. 20: 578-88. [16] Parelho, V., et al., Cell, 2008. 132: p. 422-33. [17] Chernukhin, I., et al., Mol Cell Biol, 2007. 27: 1631-48. [18] Visel, A. et al., Nature, 2009. 461: 199-205. [19] Visel, A., et al., Nature, 2009. 457: 854-8. [20] Taatjes, D. J., Trends Biochem Sci, 2010. 35: p. 315-22. [21] Gause, M. et al., Bioessays, 2008. 30: 715-8. [22] Maeshima, K. & U. K. Laemmli, Dev Cell, 2003. 4: 467-80. [23] Galande, S., et al., Curr Opin Genet Dev, 2007. 17: 408-14. [24] Torrano, V., et al., Journal of Cell Science, 2006. 119: 1746-59. [25] Sato, K., et al., J Biol Chem, 2004. 279: 30919-22. [26] Lieberman-Aiden, E., et al., Science, 2009. 326: 289-93. [27] Fullwood, M. J., et al., Nature, 2009. 462: 58-64. [28] Duan, Z., et al., Nature, 2010. 465: 363-7. [29] Guo, F., et al., Proc Natl Acad Sci USA, 1999. 96: 7143-8. [30] Lefrancois, P., et al., BMC Genomics, 2009. 10: 37. [31] Harismendy, O., et al., Genome Biol, 2009. 10: R32. [32] Li, J., et al, Genome Biol, 2010. 11: R50. [33] Paschou, P., et al., PLoS Genet, 2007. 3: 1672-86. [34] Harrison, C. J. et al., J Cell Sci, 1982. 56: 409-22. [35] Liu, X., et al., J Biol Chem, 1999. 274: 13836-40. [36] Widlak, P. & W. T. Garrard, Biochem Cell Biol, 2006. 84: 405-10. [37] Goren, A. et al., Nature Methods, 2009. 7: 47-49. [38] Hawkins, R. D., et al, Nat Rev Genet, 2010. 11: 476-486. [39] Yang, M., et al., Mol Cell, 2006. 23: 377-87. [40] Borek, D. & Z. Otwinowski, Kinetic control of eukaryotic chromatin structure by recursive topological restraints. Nature Precedings, 2008. . . . hdl.handle.net/10101/npre.2008.2672.1

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A method for processing DNA fragments, comprising:
ligating in a single reaction dN-tailed, cross-linked DNA fragments to four duplex adapters: R1 and R2 recombination adapters and S1 and S2 sequencing adapters, wherein the recombination adapters each contain a site-specific recombinase target site and R1 contains an affinity tag.

2. The method of claim 1 further comprising subsequent steps of:
recombining the target sites with a corresponding site-specific recombinase;
isolating recombined fragments comprising the affinity tag;

amplifying by PCR the recombined fragments comprising the affinity tag with primers complementary to the sequencing adapters; and sequencing the amplified PCR product.

3. The method of claim 1 further comprising antecedent steps of:

fragmenting cross-linked chromatin into 300-600 bp fragments; and blunt ending and dN tailing the fragments.

4. The method of claim 1 further comprising antecedent steps of:

fragmenting cross-linked chromatin into 300-600 bp fragments; and blunt ending and dN tailing the fragments; and subsequent steps of:

recombining the target sites with a corresponding site-specific recombinase;

isolating recombined fragments comprising the affinity tag;

amplifying by PCR the recombined fragments comprising the affinity tag with primers complementary to the sequencing adapters; and sequencing the amplified PCR product.

* * * * *